United States Patent
Ashburn

[19]
[11] Patent Number: 5,967,983
[45] Date of Patent: Oct. 19, 1999

[54] APPARATUS FOR SECURING A MEDICAL IMAGING DEVICE TO A BODY

[75] Inventor: William Ashburn, La Jolla, Calif.

[73] Assignee: Digirad Corporation, San Diego, Calif.

[21] Appl. No.: 08/550,882

[22] Filed: Oct. 31, 1995

[51] Int. Cl.⁶ .................................................. A61B 6/00
[52] U.S. Cl. ................ 600/436; 250/370.09; 250/522.1; 250/491.1
[58] Field of Search ................ 128/653.1, 897, 128/654, 659; 250/370.09, 370.08, 370.1, 370.11, 522.1, 491.1; 378/62, 63, 68, 69, 193–198; 600/407, 430, 436

[56] References Cited

U.S. PATENT DOCUMENTS

| | | | |
|---|---|---|---|
| 4,333,475 | 6/1982 | Moreno et al. | 128/711 |
| 4,632,123 | 12/1986 | Govaert et al. | 128/659 |
| 4,920,969 | 5/1990 | Suzuki et al. | 128/659 |
| 5,007,427 | 4/1991 | Suzuki et al. | 128/659 |
| 5,072,458 | 12/1991 | Suzuki | 128/659 |
| 5,111,818 | 5/1992 | Suzuki et al. | 128/659 |
| 5,337,231 | 8/1994 | Nowak et al. | 128/653.1 |
| 5,365,069 | 11/1994 | Eisen et al. | 250/378.09 |
| 5,441,050 | 8/1995 | Thurston et al. | 128/659 |

*Primary Examiner*—Brian L. Casler
*Attorney, Agent, or Firm*—Fish & Richardson P.C.

[57] ABSTRACT

A system and apparatus for obtaining medical quality images of a body under stress, such as a body in motion, are disclosed. The apparatus preferably consists of a harness into which the imaging device may be removably placed and securely positioned with respect to a body part, even when the body is in motion. The system preferably further comprises a small, light weight gamma camera. The imaging device is preferably supported by a mechanism which is separate from the harness. In each embodiment of the invention, movement of the imaging device relative to the body is minimized, yet the body is permitted to move relatively freely. Methods for use of the apparatus and system to obtain medical images of a body are also described.

15 Claims, 3 Drawing Sheets

APPARATUS FOR SECURING A MEDICAL IMAGING DEVICE TO A BODY

BACKGROUND OF THE INVENTION

1. Field of the Invention

The invention relates to devices for use in imaging organs and tissues of a body. More specifically, the invention relates to an apparatus for securing such an imaging device to a body so the imaging device will remain in a fixed position relative to the body yet the body will be able to move freely during the imaging process.

2. History of the Prior Art

Imaging devices are routinely used in medicine to obtain images of body organs and tissues. Such devices include conventional "X-ray" devices, positron emission tomography (PET) detectors, single positron emission computed tomography (SPECT) detectors, fast computed tomography (cine-CT) detectors, gamma cameras, and the like. Although used in different contexts and with different organs, all imaging devices presently used in medical applications share the requirement that the body to be imaged remain as stationary as possible with respect to the device so an accurate image may be obtained.

However, it is not possible to completely immobilize the human chest and abdomen for imaging of organs such as the heart due to involuntary movement (e.g., heartbeat). To compensate for such movement, several images may be obtained from which a composite image of the organ may be extrapolated. For example, cine-CT scanners typically obtain multiple images of organs in a matter of seconds. Through mathematical calculations and image manipulation, the series of images is combined into a single image. However, the utility of the image is limited by loss of information during the image combination step and dissipation of contrast agent from spaces within the organ (e.g., cardiac ventricles).

The problem of movement is particularly acute when evaluating heart function under stress. For example, radioisotopic imaging of the heart is a routine diagnostic procedure used to evaluate patients for coronary artery disease (CAD). In patients with CAD, ventricular function and myocardial perfusion (arterial blood flow) rates may be within normal ranges at rest, but become abnormal during physical stress. For that reason, CAD is commonly evaluated immediately after the patient has exercised (e.g., the treadmill stress test) or after the patient has received drugs to simulate the effects of exercise.

However, because the heart cannot be adequately imaged while the patient is in motion, patients may be instructed to stop moving before the images are taken. Under this approach, no information is obtained directly from the heart at peak stress or while stress on the heart develops. In an effort to obtain such information, patients may be instructed to grip or press their chest against the imaging device while exercising.

The difficulties inherent in attempting to stabilize a moving body against a stationary imaging device are apparent. Not only is the patient's freedom of movement compromised, but it is not uncommon for the patient to collide with the device during motion, thus potentially compromising the latter's accuracy. Yet the alternative of moving the imaging device with the patient's body is made difficult, if not impossible, by the weight and size of such devices. Indeed, conventional Anger gamma cameras (so named after their inventor) are typically so heavy that they must be attached to a motorized gantry to allow the camera to be moved into position for imaging.

In an effort to obtain information for use in evaluating ventricular function during stress on the heart, several researchers have attempted to use radioisotopic probes to assess heart function without imaging. For example, one approach strapped such a probe directly onto the patient's chest, presumably over the position of the left ventricle. However, without images to use for confirmation, it proved difficult to be certain that the probe was properly positioned. Moreover, although such a probe could (if properly positioned) assess ventricular function in terms of ejection fraction (EF), it cannot be used to assess regional movement of the ventricular wall. Therefore, although easily moved and attached to a body, radioisotopic probes have proven to have limited usefulness.

Thus, a need exists for an apparatus which will allow medical quality images to be obtained of body organs while the body is in movement or otherwise under stress. The present invention addresses that need.

SUMMARY OF THE INVENTION

The invention is an apparatus which will securely support an imaging device on a body so that medical quality images of body organs can be obtained notwithstanding movement by the body during the imaging process. The preferred imaging device for use with the apparatus of the invention is a gamma camera, preferably one weighing less than about 30 pounds. According to the invention, the imaging device is removably attached to the body in a secure position with respect to the organ to be imaged. The combination of the inventive apparatus and preferred lightweight gamma camera permits the body to move relatively freely while images are obtained. As a result, the invention is particularly useful for obtaining images of the body under maximum stress; e.g., to obtain images of the heart during exercise.

In one preferred embodiment of the invention, the imaging device is secured to the body by a harness. The harness is securely fastened to a body so the imaging device is immobilized over the region of the body to be imaged. Further support for the imaging device is preferably provided by means to suspend or otherwise support the imaging device in the harness.

To minimize movement of the imaging device relative to the organ to be imaged, the harness will preferably include a pocket into which the imaging device is placed. Alternatively, the imaging device may be held in place by contraction of the harness against the body.

In one aspect of the invention, the means for providing further support to the imaging device consists of a suspension mechanism comprising an adjustable weight and pulley mechanism whereby the weight of the imaging device is counterbalanced by a weight of approximately equal weight to the imaging device.

In another aspect of the invention, the weight of the imaging device is supported by an extendible bar (such as a retractable spring or gas piston) which is attached to, and supports, the imaging device.

In another aspect of the invention, the imaging device is suspended by a fixed suspension mechanism, such as a wire or beam.

In another aspect of the invention, the imaging device is supported by a bar which is pivotably mounted in balance with the weight of the imaging device.

In another aspect of the invention, the imaging device is entirely supported against the body by the harness. The preferred imaging device for use in this embodiment of the invention is one which weighs less than about 30 pounds, thus minimizing the strain of carrying the device on the body. Most preferably, the dimensions of the imaging device will be less than about 16 inches along each side.

BRIEF DESCRIPTION OF THE DRAWINGS

Like numerals refer to like elements in FIGS. 2 and 3.

DESCRIPTION OF THE PREFERRED EMBODIMENTS

Figure 1:
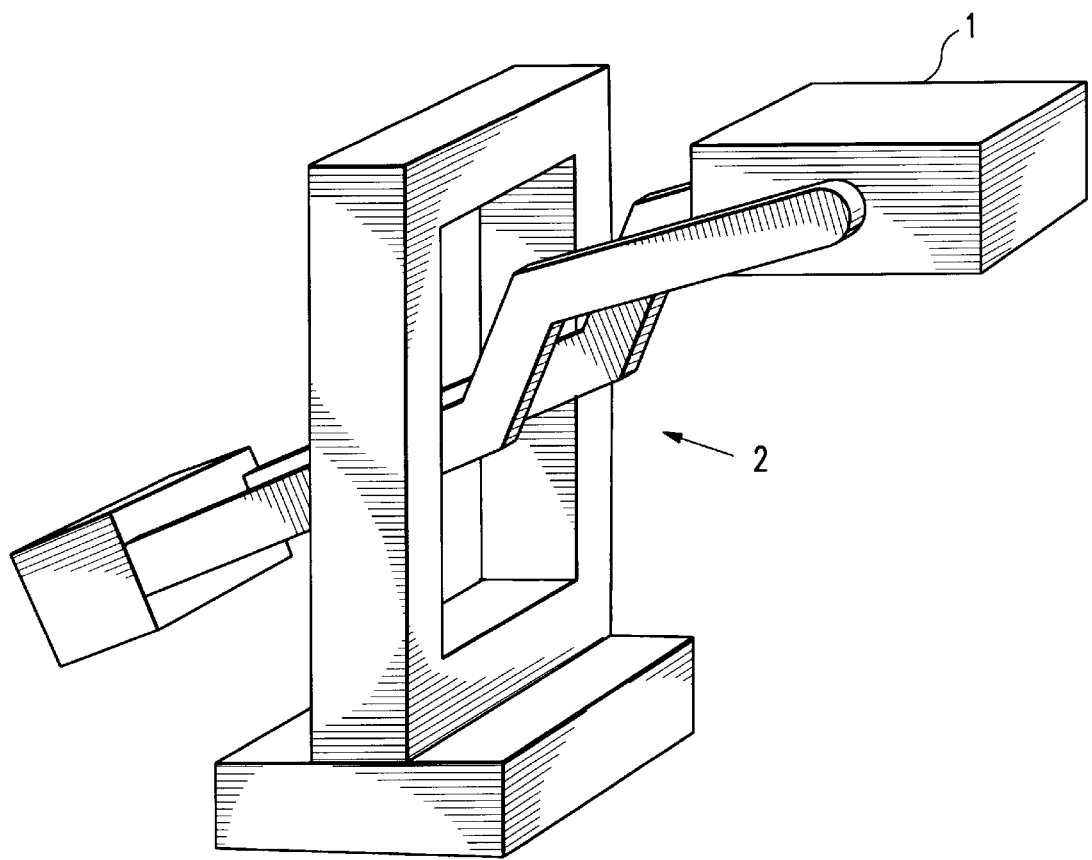
FIG. 1 is a plan view of a (prior art) Anger gamma camera with gantry.

Many of the advantages of the apparatus of the invention over prior art mechanisms for supporting an imaging device are apparent in a comparison of the invention to the prior art camera and gantry arrangement shown in FIG. 1. As shown in FIG. 1, a conventional Anger gamma camera is a large, relatively heavy imaging head 1 attached to a movable mechanical gantry 2. As a consequence of its lead shielding, device 1 may weigh in excess of several hundred pounds. Given their size and design, devices such as the one shown in FIG. 1 cannot follow movement of a patient's body.

For comparison, imaging devices used with the invention are removably secured to a body to be imaged in such a way that movement of the imaging device with respect to the body is minimized; i.e., so that medically useful images of a body part such as the heart can be obtained even though the body is in motion. For purposes of discussion, the imaging device for use with the invention will be referred to as a gamma camera, although those of ordinary skill in the art will understand that other imaging devices may also be readily used in the inventive apparatus. Also, for the sake of convenience, the description of the invention refers to use of the apparatus by a human. However, it will be understood that the apparatus may be adapted for use by other mammals, such as livestock and pet animals.

All of the embodiments of the invention share the advantage of supporting an imaging device while stabilizing it against a body. Each embodiment permits some range of movement by the body while minimizing movement of the imaging device with respect to the part of the body to be imaged. For purposes of this disclosure, movement of the body within such range of movement shall be referred to as movement "freely" by the body. The term "freely" will be understood to mean movement by the body to the fullest extent permitted by the dimensions of the inventive apparatus (e.g., the length and/or extendibility of support mechanisms present in the apparatus with respect to the radius about such support mechanism in which the body is to be moved).

As shown in the FIGS, the most common use of the apparatus of the invention will likely be to obtain first pass images of the heart (over the left ventricle), particularly during physical exercise. However, it can be readily appreciated that the apparatus of the invention may also be used to image other organs of the body. For example, if body 10 shown in the FIGS. 2–3 was facing away from rather than toward stand 20, gamma camera 5 could be positioned along the back of body 10 to image, for example, the kidneys. Thus, the invention will be understood not to be limited to use for imaging a specific organ or with a specific imaging device, but rather is defined by the scope of the appended claims.

Figure 2:
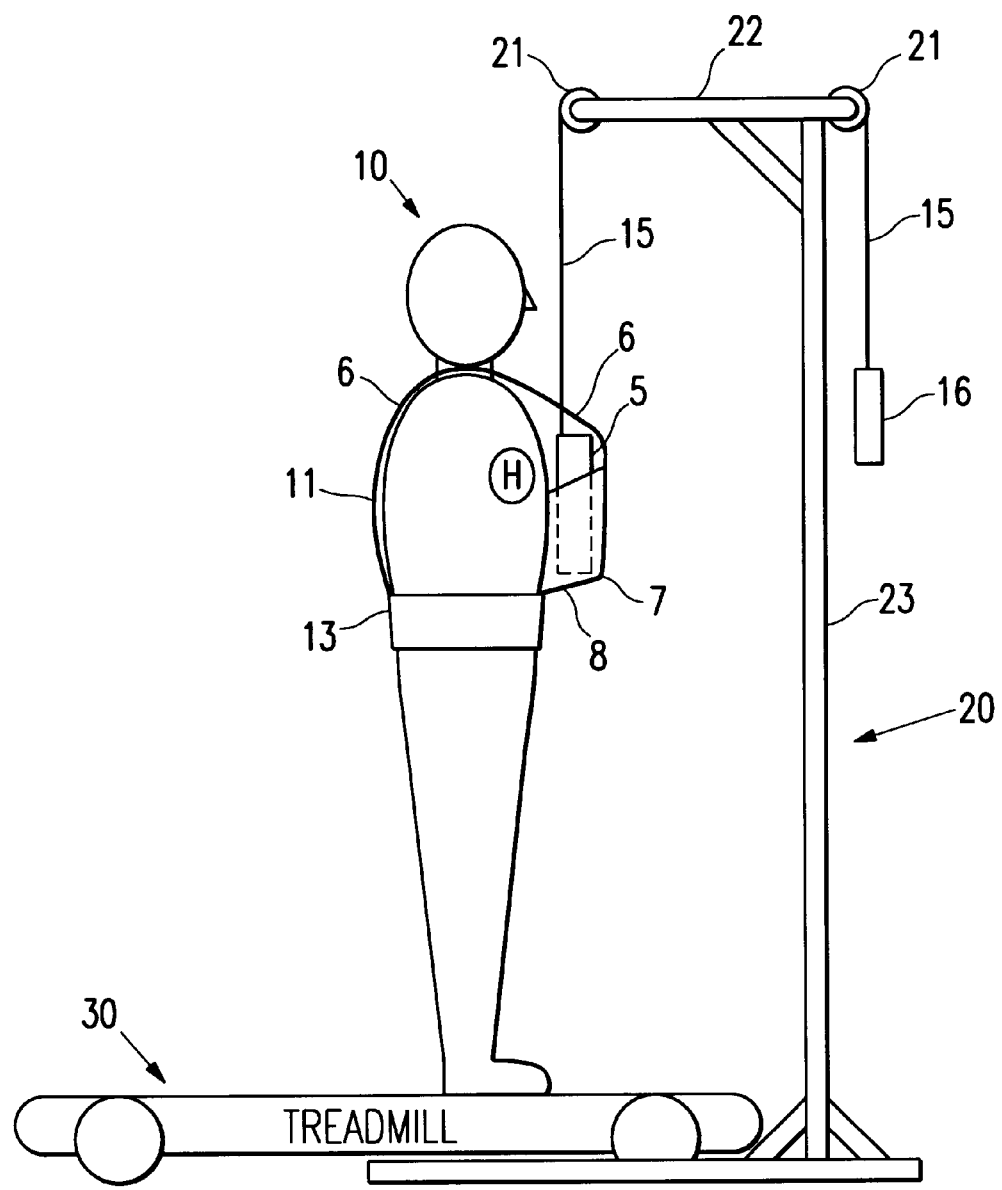
FIG. 2 is a side view of a preferred embodiment of the invention, showing the pouch and imaging device being supported by an adjustable weight and pulley system.

A preferred embodiment of the invention is shown in FIG. 2. In FIG. 2, the imaging device is represented by gamma camera 5, which is secured to a human body 10. To ease the strain of carrying the imaging device on body 10, gamma camera 5 will weigh no more than about 100 pounds, most preferably no more than about 20 pounds. Similarly, gamma camera 5 will preferably be no wider or longer than the chest of the person with whom it is to be used, which will typically be no more than about 16 inches along each side. Further, so gamma camera 5 will readily follow the body in motion, the mass of the gamma camera should not substantially exceed that of the body part against which it is placed (e.g., the chest).

Such a gamma camera is described in co-pending, commonly owned U.S. patent application Ser. No. 08/372,807 (filed Dec. 23, 1994), the disclosure of which is incorporated herein by this reference to illustrate the structure and form of a preferred imaging device for use with the apparatus of the invention. A commercial embodiment of the gamma camera claimed in the '807 Application is also being made available by DIGIRAD, Inc. of San Diego, Calif.

Figure 3:
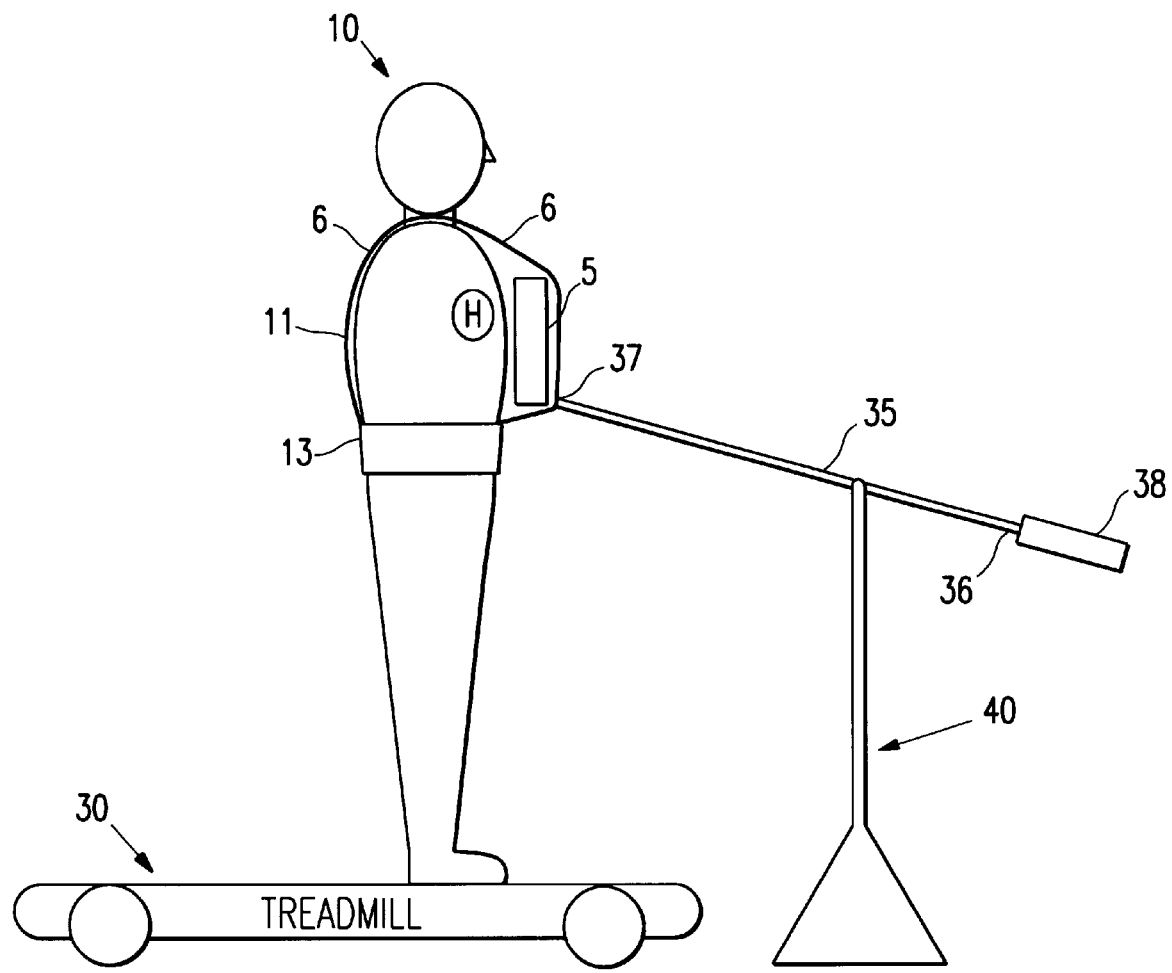
FIG. 3 is a side view of an alternative embodiment of the invention, showing the weight of the imaging device being supported by a pivotable bar.

For use with the inventive apparatus, gamma camera 5 is placed into harness 6. Harness 6 may secure camera 5 against body 10 by contraction of a piece of fabric stretched snugly over gamma camera 5 in at least two opposing directions (to form a strap) or may cover gamma camera 5 as shown in FIG. 3. The camera may also be placed snugly within a sack-like structure in the front of the harness (e.g., a pocket 7, containing the camera shown partially in phantom in FIG. 2).

Preferably, harness 6 will be a relatively durable material, such as cotton canvas, plastic, rubber or nylon. Also, depending on the structure of the imaging device, harness 6 may also include a rigid cup or bracket at the posterior end of pocket 7 into which the imaging device will be seated. Any such rigid cup or bracket may be attached to the posterior of pocket 7 by any suitable fastening means, such as snaps or stitching. Alternatively, where camera 5 is secured within harness 6 by a stretch of fabric as shown in FIG. 2, any rigid cup or bracket present will be attached by suitable fastening means to the inner surface of harness 6 so as to extend beneath, and provide additional stability to, the posterior end of gamma camera 5.

So pocket 6 may be adjusted to fit onto different size bodies at desired locations, it will preferably be secured to body 10 by adjustable attachment means, such as slidable straps. For example, as shown in FIG. 2, harness 6 is attached to body 10 by adjustable straps 11 which extend over each shoulder and connect to a belt 13 intended to circle the waist. The posterior end 8 of pocket 7 is securely attached to belt 13 in a removable or permanent fashion. For better support and comfort, belt 13 is preferably a lumbar support belt; i.e., a belt which is sufficiently wide to encompass the lumbar region of the wearer's back. When fitted tight around the waist, a lumbar support belt will provide support to the wearer's lower back. Such belts are commercially available and well-known in the art for medical and industrial uses.

For additional stability, harness 6 may also be secured to body 10 by additional attachment means, such as straps extending beneath the wearer's arms which attach to straps 11 behind the wearer's back, and may also extend completely around the wearer's back. Any such straps used as attachment means will preferably be adjustable by use of adjustment means such as slides, buckles or fastening fabric (e.g., VELCRO® adhesive tape) so the straps may be fixed in place on body 10.

Other configurations of harness 6, as well as alternative attachment means, will be apparent to those of ordinary skill in the art. For example, harness 6 may be attached to the body as part of a fitted vest or jacket. Further, to ensure proper positioning of gamma camera 5, it may be secured in a fixed position within harness 6 by fasteners such as VELCRO® fasteners to attach the camera to the patient's chest. For example, where harness 6 includes a sack-like structure such as pocket 7, fasteners may be mated between the outer surface of pocket 7 (between the pouch and the body) and a surface between pocket 7 and the body (such as a strap or inner vest). Alternatively, where the camera is secured within harness 6 by contraction of a stretch of fabric larger in diameter than the camera, the fabric will extend around the camera in at least two directions and attach directly to a surface (such as a strap or inner vest) worn on the body. For example, gamma camera 5 may be placed between the front surface of harness 6 and the body. Using a VELCRO®-type hook and loop fabric fastener, the inner surface of the front of harness 6 which extends beyond camera 5 would then be secured to body 10 by joining the fabric fasteners on harness 6 to complementary fabric fasteners attached to a cloth vest worn on the body. Gamma camera 5 can be secured more closely to the body by tightening harness 6 around the body's girth.

Advantageously, the inventive apparatus is used to retain a gamma camera at a desired point with respect to body 10 while body 10 is in movement during, for example, a cardiac stress treadmill test. To relieve the body being imaged of the camera's weight while the body is under stress, substantially all of the weight of the camera is supported by one or more of the means for supporting the camera described below.

A preferred embodiment to provide support to gamma camera 5 by a mechanism separate from the harness is shown in FIG. 2. According to this embodiment, gamma camera 5 is suspended in harness 6 from a rope (preferably a flexible wire or the like) 15 hanging from a structure raised above body 10, such as the vertical arm 22 of the stand 20 shown in FIG. 2. Opposite its attachment to vertical arm 22, rope 15 is connected to gamma camera 5 by any fastener of sufficient strength to support gamma camera 5 (notwithstanding moderate movement of body 10).

To accommodate movement by body 10, rope 15 is preferably slidably engaged with one or more pulleys along vertical arm 22 of stand 20 to allow rope 15 to shorten and lengthen as required to accommodate movement of body 10 (for example, on exercise equipment such as treadmill 30, a stairstepper or indoor bicycle).

To balance gamma camera 5, a counterweight 16 is attached to rope 15 opposite the point of attachment of gamma camera 5; i.e., so that counterweight 16 hangs from rope 15 along vertical spine 23 of stand 20. Thus, although movement of body 10 is accommodated by movement of rope 15, gamma camera 5 is stabilized in position in harness 6 by the tendency of the camera and counterweight 16 to remain in equilibrium (i.e., balance) with respect to one another as well as by compression of the camera against body 10.

Gamma camera 5 may also be suspended from vertical arm 22 by a length of extendible material, preferably a spring, an elastic cord, or a highly compressible and extendible gas piston (e.g., such as the hydraulic cylinders commonly used to permit the "steps" of stairstepper exercise machines to be compressed then returned to a neutral position). In this embodiment of the invention, pulleys 21 will not be included on stand 20. Instead, movement by body 10 will be accommodated by flex, compression and extension of the spring or other extendible material. Alternatively, harness 6 may be attached to vertical arm 22 by any of the means described above in lieu of suspending gamma camera 5 from vertical arm 22.

The weight of gamma camera 5 can also be relieved by providing support from below the camera. An example of a preferred support stand 40 for use in this embodiment of the invention is shown in FIG. 3. In FIG. 3, a bar 35 is pivotably mounted on stand 40 at a midpoint between the distal end 36 and proximal end 37 of the bar. Preferably, bar 35 will be mounted on stand 50 so bar 35 may extend upward to about a 45° angle from vertical at its proximal end. Proximal end 37 is detachably attached to harness 6 at its bottom or midpoint. Camera 5 will be stabilized in position against body 10 by tightening of harness 6 and may be further stabilized by attachment of camera 5 to rope 15 (with or without counterbalance) or to a extendible material (such as a spring or elastic cord).

To balance the weight of camera 5, a counterbalance 38 of about equal weight to camera 5 will be attached to distal end 36 of bar 35. Further, being pivotably mounted on stand 40, bar 35 will move upward and downward in response to movement by body 10. Thus, this embodiment of the invention is particularly well suited for use with exercise equipment that may cause vertical movement of the body, such as a stairstepper apparatus.

The invention having been fully described, modifications thereto which meet the intended use and scope of the invention will become apparent to those of ordinary skill in the art. All such modifications are within the scope of the invention being claimed.

What is claimed is:

1. A system for obtaining medical images of a body in motion comprising:

(a) a harness for removably securing and supporting a gamma camera on a body in motion so that the body may move freely yet movement of the gamma camera relative to the body is minimized; and, (b) a gamma camera adapted to be secured against the body by the harness, wherein the gamma camera has dimensions of less than about 16 inches on each side and includes a collimator, an imaging detector that produces electrical pulses of amplitude indicative of a magnitude of radiation absorbed from photons of x-ray or gamma-ray radiation, and means for processing the electrical pulses.

2. The system according to claim 1 wherein the harness is adjustable to secure the device over the left ventricle of the body's heart.

3. An apparatus comprising:

(a) a harness for removably securing a gamma camera on a body so that movement of the gamma camera relative to the body is minimized, wherein the gamma camera includes a collimator, an imaging detector that produces electrical pulses of amplitude indicative of a magnitude of radiation absorbed from photons of x-ray or gamma-ray radiation, and means for processing the electrical pulses; and, (b) a mechanism separate from the harness for supporting the gamma camera in the harness, wherein the mechanism for supporting the gamma camera is capable of supporting substantially all of the weight of the gamma camera and permits the body to move freely.

4. The apparatus according to claim 3 wherein the harness is attachable to the body by adjustable straps.

5. The apparatus according to claim 3 wherein the harness is attachable to the body by an adjustable belt which is extendable around the girth of the body.

6. The apparatus according to claim 3 further comprising exercise equipment for placing the body under physical stress.

7. The apparatus according to claim 3 wherein the harness is adjustable to place the device over the left ventricle of the body's heart.

8. An apparatus for securing a medical imaging device to a mammalian body comprising:
   (a) a harness for removably securing an imaging device on a body so that movement of the device relative to the body is minimized; and,
   (b) a mechanism separate from the harness for supporting the imaging device when placed into the harness,
   wherein the mechanism for supporting the imaging device comprises a stand and a bar pivotably mounted thereon, wherein further the bar has a proximal end attached to the harness such that the mechanism is capable of supporting substantially all of the weight of the imaging device and permits the body to move freely.

9. The apparatus according to claim 8 wherein the bar is pivotable to about 45° from vertical at the proximal end.

10. A method for obtaining medical images of a part of a body from which such images may be obtained, comprising:
    (a) securing a gamma camera in a harness removably attached to a body, wherein the gamma camera has dimensions of no more than about 16 inches on each side and includes a collimator, an imaging detector that produces electrical pulses of amplitude indicative of a magnitude of radiation absorbed from photons of x-ray or gamma-ray radiation, and means for processing the electrical pulses;
    (b) adjusting the harness so the gamma camera is positioned over the body part to be imaged;
    (c) allowing the body to move freely; and,
    (d) obtaining images of the body part to be imaged.

11. A method according to claim 10 wherein the body part to be imaged is the heart and the imaging device is securely positioned over the left ventricle of the heart.

12. A method according to claim 11 wherein the body is placed under physical stress while the images are obtained.

13. A method for obtaining medical images of a part of a body from which such images may be obtained, comprising:
    (a) securing an imaging device comprising a gamma camera in a harness removably attached to a body, wherein the gamma camera has dimensions of no more than about 16 inches on each side and includes a collimator, an imaging detector that produces electrical pulses of amplitude indicative of a magnitude of radiation absorbed from photons of x-ray or gamma-ray radiation, and means for processing the electrical pulses;
    (b) supporting the imaging device in the harness with a mechanism separate from the harness for providing such support, wherein the mechanism for providing support is capable of supporting substantially all of the weight of the imaging device;
    (c) adjusting the harness so the gamma camera is positioned over the body part to be imaged;
    (d) allowing the body to move freely; and,
    (e) obtaining images of the body part to be imaged.

14. A method according to claim 13 wherein the body part to be imaged is the heart and the imaging device is securely positioned over the left ventricle of the heart.

15. A method according to claim 14 wherein the body is placed under physical stress while the images are obtained.

* * * * *